United States Patent
Williams

(10) Patent No.: US 6,596,919 B2
(45) Date of Patent: Jul. 22, 2003

(54) SIGNAL STRING TAMPON

(75) Inventor: Karla E Williams, Westwood, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/771,175

(22) Filed: Jan. 26, 2001

(65) Prior Publication Data

US 2003/0120227 A1 Jun. 26, 2003

(51) Int. Cl.[7] .................................................. A61F 13/15
(52) U.S. Cl. .................... 604/361; 604/385.18; 604/904
(58) Field of Search ........................... 604/904, 385.17, 604/385.18

(56) References Cited

U.S. PATENT DOCUMENTS

| 3,589,364 A | * | 6/1971 | Dean et al. | |
|---|---|---|---|---|
| 3,756,238 A | | 9/1973 | Hanke | |
| 3,794,024 A | | 2/1974 | Kokx et al. | 128/285 |
| 3,796,219 A | | 3/1974 | Hanke | |
| 4,317,454 A | | 3/1982 | Bucalo | 128/759 |
| 5,647,863 A | | 7/1997 | Hammons et al. | |
| 5,649,914 A | | 7/1997 | Glaug et al. | 604/361 |
| 5,681,298 A | | 10/1997 | Brunner et al. | 604/361 |
| 5,702,376 A | | 12/1997 | Glaug et al. | 604/361 |
| 5,728,125 A | | 3/1998 | Salinas | 604/361 |
| 5,769,813 A | * | 6/1998 | Peiler et al. | 604/11 |
| 5,797,892 A | | 8/1998 | Glaug et al. | 604/361 |
| 5,840,055 A | * | 11/1998 | Sgro | 604/11 |

FOREIGN PATENT DOCUMENTS

GB          1433415          4/1976

* cited by examiner

*Primary Examiner*—Dennis Ruhl
(74) *Attorney, Agent, or Firm*—Ohlandt, Greeley, Ruggiero & Perle, LLP

(57) ABSTRACT

There is provided a tampon that comprises an absorbent pledget and a removal string having a menstrual fluid indicator associated therewith. The absorbent pledget has a proximal end that is placed near the cervical bone and a distal end opposite the proximal end. The indicator is formed on or in the removal string. Preferably, the indicator is formed over the entire length and circumference of the removal string. The indicator provides a sensory signal to the user when the capacity of the absorbent pledget of the tampon is exhausted, or when by-pass leakage is about to commence.

16 Claims, 1 Drawing Sheet

SIGNAL STRING TAMPON

BACKGROUND OF THE INVENTION

1. Field of the Invention

The present invention relates generally to catamenial devices or tampons. More particularly, the present invention relates to catamenial devices or tampons adapted to signal the user. The present invention further relates to catamenial devices or tampons in which the string or other tampon removal device of the tampon signals the user upon exhaustion of the absorbent pledget and/or before commencement of by-pass leakage.

Presently, women have to remove the tampon to determine whether it has been used to capacity. Even if not completely used, the tampon usually is not reinserted. Generally, a woman removes a tampon before it has reached its capacity in order to prevent an accident. Namely, if the capacity is exceeded, the excess menses flows, unimpeded from the vagina, to soil the user's clothing.

One criteria for determining when to remove a tampon is the elapsed time from insertion. However, the elapsed time criteria is not satisfactory for several reasons. First, the menstrual flow rate varies throughout the menstrual period. Thus, much of the absorbent capacity of a tampon is wasted due to the tendency to change the tampon to avoid accidental leakage. Secondly, flow variations throughout the menstrual period cause problems as to how long to wear a tampon since a woman cannot establish a definite time period in which the absorbent capacity of a tampon is sufficient. Third, occasionally menses leaks before the tampon nears its full potential absorbency. This is generally known as by-pass leakage. This leakage is usually not predictable by the user's habitual wearing time. Therefore, a woman is in a quandary as to how long to wear the tampon during the varying menstrual flow days.

Larger and more absorbent tampons permit a woman to change tampons less often. However, larger tampons do not approach the goal of fully exhausting the absorbent capacity of the tampon and preventing accidents due to by-pass leakage.

2. Description of the Prior Art

Attempts have been made to provide a signal to a user when a sensory indicator is contacted by a body fluid. For example, U.S. Pat. Nos. 5,649,914, 5,702,376, and 5,797,892 issued to Glaug et al., on Jul. 22, 1997, Dec. 30, 1997, and Aug. 25, 1998, respectively, describe a toilet training aid. The aid is in the form of a pad that creates a temperature change sensation, a wet sensation, a dimensional change sensation, or a combination thereof when contacted by urine. Another example of a toilet training aid pad with a temperature change sensation signal is described in U.S. Pat. No. 5,681,298, to Brunner et al., that issued on Oct. 28, 1997.

There have been attempts to detect the presence of menstrual fluids. For example, U.S. Pat. No. 5,647,863, to Hammons et al., that issued on Jul. 15, 1997, describes a sanitary napkin. The napkin provides a signal by way of an indicator member that becomes noticeably stained when the storage capacity of the sanitary napkin is substantially exhausted. U.S. Pat. No. 5,728,125, to Salinas, that issued on Mar. 17, 1998, describes a sanitary napkin having a temperature-sensitive reactive chemical product that can respond by turning cold when it contacts and dissolves in a menstrual flow.

What is needed in the art is a tampon that provides the user with a signal when the tampon has reached its maximum absorbent capacity, or is about to leak even though the tampon is not at full capacity, as a result of by-pass leakage.

SUMMARY OF THE INVENTION

It is an object of the present invention to provide a tampon that has signal means.

It is another object of the present invention to provide such a tampon in which the string has the signal means that alerts the user when the tampon's absorbent capacity is exhausted.

It is yet another object of the present invention to provide such a tampon having a removal string with a sensual, absorbent capacity signal associated therewith.

It is also another object of the invention to provide such a tampon with a string that alerts the user that by-pass leakage about to commence.

These and other objects of the present invention are achieved by a tampon that comprises an absorbent pledget and a removal string having a menstrual fluid indicator associated therewith. The absorbent pledget has a proximal end that is placed near the cervical bone and a distal end opposite the proximal end. The indicator is preferably formed on or in the removal string. In a more preferred embodiment, the indicator is formed over the entire length and circumference of the removal string. The indicator is designed to provide a sensory signal to the user when the capacity of the absorbent pledget of the tampon is exhausted or when by-pass leakage is about to commence.

DESCRIPTION OF THE INVENTION

Figure 1:
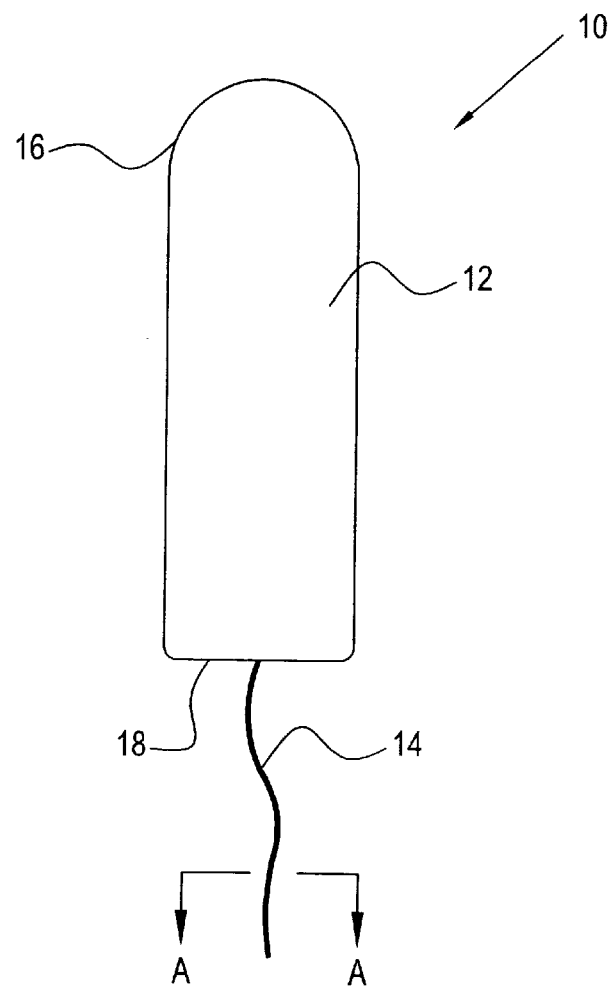
FIG. 1 is a plan view of a tampon according to the present invention.

Referring to FIG. 1, there is provided a tampon 10 having an absorbent pledget 12 and a removal string 14 connected to the pledget. The string 14 has a menstrual fluid indicator associated therewith. The absorbent pledget 12 has a proximal end 16 that, in use, is positioned near the cervical bone and a distal end 18 opposite the proximal end.

Figure 2:
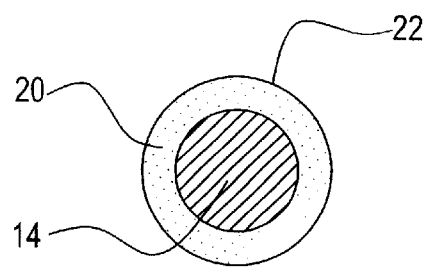
FIG. 2 is a cross-sectional view taken along line A—A in FIG. 1.

Referring to FIG. 2, in one embodiment of the present invention, the indicator 20 may be applied to the removal string 14 as a coating 22. The coating 22 may cover only the portion of the removal string 14 near the distal end 18 of the pledget 12. Preferably, the coating 22 is along the entire length and circumference of the removal string 14. The coating 22 may be applied to the removal string 14 either before or after the string is attached to the pledget 12, by any method known to those skilled in the art. These methods include, for example, padding, foaming, and spraying.

In another embodiment of the present invention, the indicator may include a fiber or blend of fibers with sensory capabilities woven into the string during its manufacture. By way of example, the indicator may simply be carded or randoed fiber or a web of rayon fiber, curly fiber, superabsorbent polymer (SAP) fiber, and combinations thereof.

The indicator is designed to provide a sensory signal to the user that the capacity of the absorbent pledget of the tampon is exhausted and/or that by-pass leakage is about to commence.

The indicator is activated by menstrual fluid such that the activation of the indicator is perceivable to the user while the tampon remains in the vagina. Thus, the indicator becomes sensual to the user when wetted by menstrual fluid thereby avoiding removal of the tampon until essentially the entire capacity of the absorbent pledget is exhausted and/or just prior to commencement of by-pass leakage.

The material in the signal layer that provides the signal or sensory indication may be directly included or woven into the removal string during its manufacture. This material may include fibers or materials that tend to "spring open", or swell, in the presence of moisture. Suitable fibers or materials include, for example, curly fiber, cellulosic sponge, swellable absorbent material such as superabsorbent polymer (SAP), hydrogel, or any combination thereof. The "opening" or swelling of these materials in the removal string, and the resulting sensation of pressure, signal the user that the capacity of the absorbent pledget of the tampon is exhausted, and/or that by-pass leakage may occur.

In addition to signaling the user, the curly fiber, cellulosic sponge, and superabsorbent polymer, in the removal string may provide further leakage protection due to their "opening" and swelling properties. Therefore, even if the user fails to or is unable to immediately remove and replace the tampon upon being signaled that it should be removed, this added leakage protection feature serves as a further preventative measure against by-pass leakage.

In one embodiment, the signal layer may include exothermic materials that release heat upon exposure to moisture. Thus, when menstrual fluid contacts the signal layer, heat is released producing a sensation of warmth, signaling the user that the capacity of the absorbent pledget is exhausted, and/or that by-pass leakage may commence. Suitable exothermic materials include, for example, Cabsorb ZS500A, an exothermic zeolite provided by GSA, glycerin, and mixtures thereof.

In another embodiment, the signal layer may also include a material that produces a cold sensation. As menstrual fluid contacts the signal layer, a cold sensation is produced signaling the user that the capacity of absorbent pledget is exhausted, and/or that by-pass leakage may commence. Suitable materials include, for example, Optacool and Frescolat ML, both provided by H&R Florasynth, menthol, ethanol, and mixtures thereof.

In a third embodiment, the signal layer may also include a gas-releasing material. As menstrual fluid contacts the signal layer, gas is released that produces a "fizzy" sensation again signaling the user that the capacity of the absorbent pledget is exhausted, and/or that by-pass leakage may commence. Suitable gas releasing materials include, for example, sodium bicarbonate.

In a fourth embodiment, the signal layer may also include a color producing material. As menstrual fluid contacts the signal layer, a distinct color is produced signaling the user that the capacity of the absorbent pledget is exhausted, and/or that by-pass leakage may commence.

In a fifth embodiment, the signal layer may also include an encapsulated fragrance-releasing material. As menstrual fluid contacts the signal layer, the encapsulated fragrance is released signaling the user that the capacity of the absorbent pledget is exhausted, and/or that by-pass leakage may commence.

In addition, encapsulation is not limited to fragrance. Each and every sensory material described above may be present in an encapsulated form, either alone or in combination. As menstrual fluid contacts the encapsulated sensory material, the sensory material is released, signaling the user that the capacity of the absorbent pledget is exhausted, and/or that by-pass leakage may commence.

The present invention having been thus described with particular reference to the preferred forms thereof, it will be obvious that various changes and modifications may be made therein without departing from the spirit and scope of the present invention as defined in the appended claims.

I claim:

1. A tampon comprising:
   an absorbent pledget having a proximal end for placement near the cervical bone of a user and a distal end opposite said proximal end; and
   a removal string being connected to said absorbent pledget, said removal string having a menstrual fluid indicator in contact with said removal string at said distal end, said indicator being sensually perceivable to the user when contacted by a menstrual fluid,
   wherein said indicator has a sensory material that reacts in the presence of the menstrual fluid,
   wherein said sensory material is selected from the group consisting of:
   (a) gas-releasing material;
   (b) fragrance-releasing material;
   (c) spring openable material selected from the group consisting of curly fiber, cellulosic sponge, and any combinations thereof;
   (d) any mixture of (a)–(c) above.

2. The tampon of claim 1, wherein said gas-releasing material is sodium bicarbonate.

3. The tampon of claim 1, wherein said sensory material is encapsulated.

4. The tampon of claim 1, wherein said sensory material is included in said removal string during its manufacture.

5. A string for a tampon, the string having a menstrual fluid indicator in contact with the string, said indicator being sensually perceivable to a user when contacted by a menstrual fluid,
   wherein said indicator has a sensory material that reacts in the presence of the menstrual fluid, and
   wherein said sensory material is selected from the group consisting of:
   (a) gas-releasing material;
   (b) fragrance-releasing material;
   (c) spring openable material selected from the group consisting of curly fiber, cellulosic sponge, and any combinations thereof;
   (d) any mixture of (a)–(c) above.

6. The tampon of claim 5, wherein said gas-releasing material is sodium bicarbonate.

7. The tampon of claim 5, wherein said sensory material is encapsulated.

8. A method for avoiding by-pass leakage comprising:
   (a) providing a tampon having a removal string with a menstrual fluid indicator, whereby said indicator is sensually perceivable to a user when contacted by menstrual fluid; and
   (b) removing said tampon once said user sensually perceives said indicator,
   wherein said indicator has a sensory material that reacts in the presence of said menstrual fluid, and
   wherein said sensory material is selected from the group consisting of:
   (1) gas-releasing material;
   (2) fragrance-releasing material;

(3) spring openable material selected from the group consisting of curly fiber, cellulosic sponge, and any combinations thereof;

(4) any mixture of (1)–(3) above.

9. The tampon of claim 8, wherein said gas-releasing material is sodium bicarbonate.

10. The tampon of claim 8, wherein said sensory material is encapsulated.

11. A process for making a removal string having a menstrual fluid indicator comprising applying a sensory material to said string, wherein said sensory material reacts in the presence of menstrual fluid, and wherein said sensory material is selected from the group consisting of:
(a) gas-releasing material;
(b) fragrance-releasing material;
(c) any mixture of (a)–(b) above.

12. The process of claim 11, wherein said sensory material is applied to said string either before or after said string is secured to a tampon pledget.

13. The tampon of claim 11, wherein said gas-releasing material is sodium bicarbonate.

14. The tampon of claim 11, wherein said sensory material is encapsulated.

15. A process for making a removal string having a menstrual fluid indicator comprising fabricating said string with a sensory material, wherein said sensory material reacts in the presence of menstrual fluid, and wherein said sensory material is selected from the group consisting of curly fiber, cellulosic sponge, and any combinations thereof.

16. The process of claim 15, wherein said sensory material is woven into said string.

* * * * *

UNITED STATES PATENT AND TRADEMARK OFFICE
CERTIFICATE OF CORRECTION

PATENT NO. : 6,596,919 B2
DATED : July 22, 2003
INVENTOR(S) : Karla E. Williams

It is certified that error appears in the above-identified patent and that said Letters Patent is hereby corrected as shown below:

Column 4,
Line 50, "The tampon of" should read -- the string of --.

Column 5,
Lines 5 and 7, "The tampon of" should read -- The method of --.

Column 6,
Lines 4 and 6, "The tampon of" should read -- The process of --.

Signed and Sealed this

Twenty-seventh Day of September, 2005

JON W. DUDAS
*Director of the United States Patent and Trademark Office*